United States Patent [19]

Jordan et al.

[11] Patent Number: 4,858,607
[45] Date of Patent: Aug. 22, 1989

[54] PLASTIC DEVICE FOR INJECTION AND OBTAINING BLOOD SAMPLES

[75] Inventors: Pavel Jordan; Janet Muff, both of So. Pasadeana; Bernard Strong, Tarzana, all of Calif.

[73] Assignee: Pavel Jordan & Associates, Garden Grove, Calif.

[21] Appl. No.: 108,950

[22] Filed: Oct. 16, 1987

[51] Int. Cl.⁴ ............................................. A61B 17/34
[52] U.S. Cl. .................................. 128/314; 128/329 R
[58] Field of Search ......................... 128/329 R, 314; 604/134, 136–138, 117, 156, 157

[56] References Cited

U.S. PATENT DOCUMENTS

| 2,047,010 | 7/1936 | Dickinson | 604/157 |
| 2,664,086 | 12/1953 | Transue | 604/157 |
| 2,679,843 | 6/1954 | May | 604/156 |
| 2,701,566 | 2/1955 | Krug | 604/156 |
| 3,030,959 | 4/1962 | Grünert | 128/329 R |
| 3,330,279 | 7/1967 | Sarnoff et al. | 604/138 |
| 4,194,505 | 3/1980 | Schmitz | 604/138 |
| 4,203,446 | 5/1980 | Höfert et al. | 128/329 R |
| 4,375,815 | 3/1983 | Burns | 128/329 R |
| 4,445,510 | 5/1984 | Rigby | 128/329 R |
| 4,527,561 | 7/1985 | Burns | 128/314 |
| 4,530,695 | 7/1985 | Phillips et al. | 604/134 |
| 4,677,979 | 7/1987 | Burns | 128/314 |

FOREIGN PATENT DOCUMENTS

| 1269771 | 6/1968 | Fed. Rep. of Germany | 604/117 |
| 1107099 | 12/1955 | France | 604/157 |

Primary Examiner—John D. Yasko
Assistant Examiner—Ralph Lewis
Attorney, Agent, or Firm—Willie Krawitz

[57] ABSTRACT

An inexpensive injection device is provided which is manufactured of plastic components, and is adapted to fit various syringe sizes. The injection device is spring loaded, and provides a firing barrel which, in the cocked position, is offset slightly from the central bore of the device.

When the device is fired, the firing barrel is aligned with the central bore and projects the needle portion of the syringe into the user.

For obtaining blood samples, the syringe is replaced by a striker element, which actuates a spring loaded puncture module which punctures the skin and is quickly withdrawn.

2 Claims, 4 Drawing Sheets

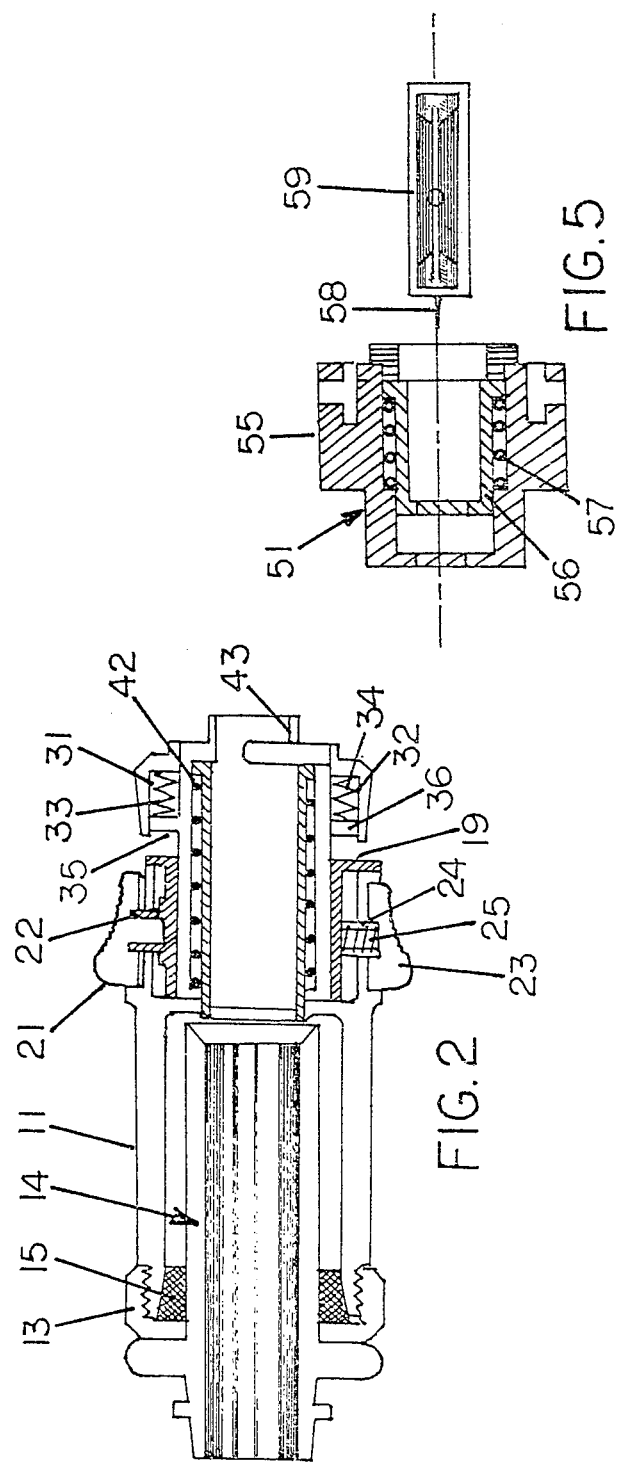

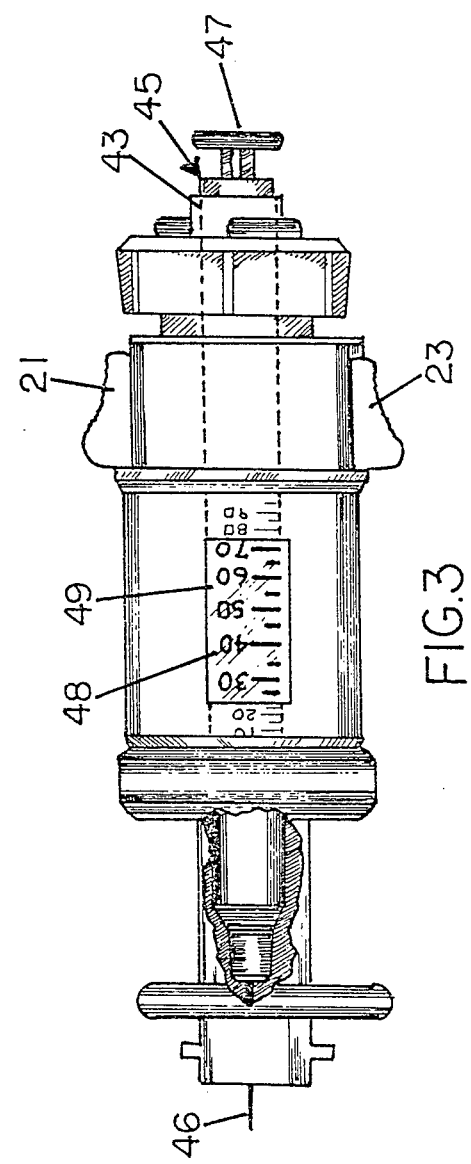

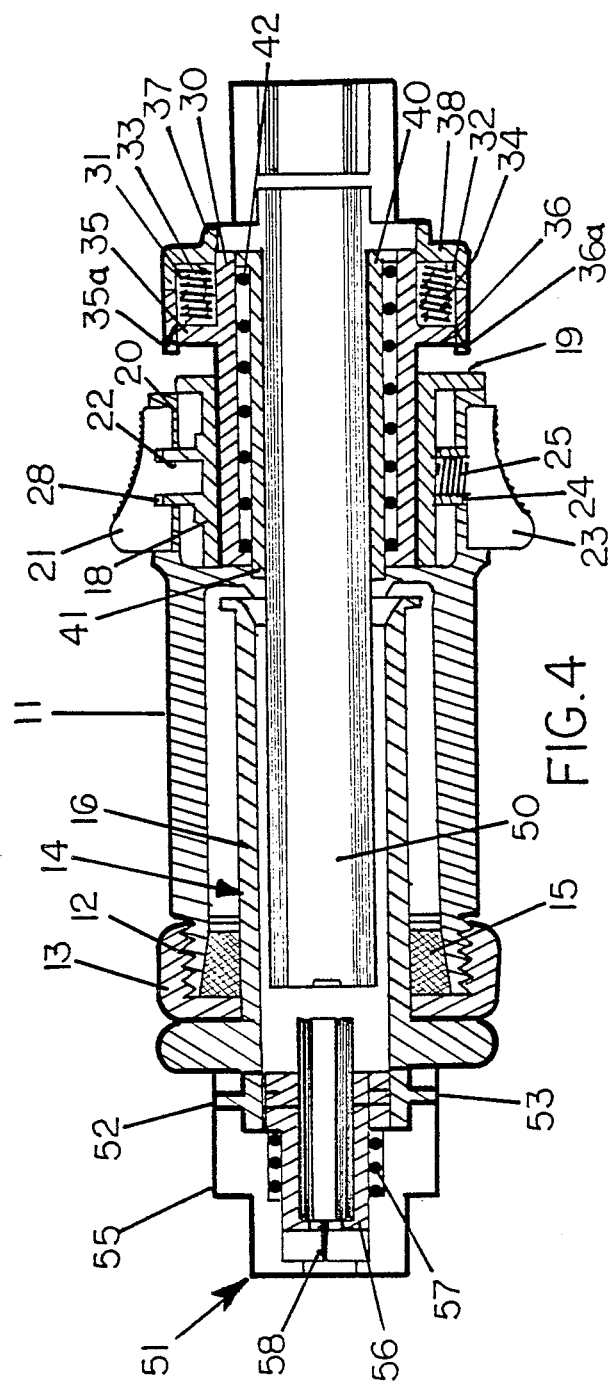

PLASTIC DEVICE FOR INJECTION AND OBTAINING BLOOD SAMPLES

BACKGROUND OF THE INVENTION

This invention relates to a pla;tic injector device which may be loaded, cocked and fired with ease. The injector may be readily applied to any part of the user's body to obtain an accurate injection site. The device may also be readily modified to obtain blood samples, and functions in the same mode as the injector.

Many patents disclose the use of hypodermic injector devices, such as U.S. Pat. No. 4,601,708 by Pavel Jordan, to the assignee, herein. The '708 patent is a highly durable device constructed of stainless steel and is quite effective. However, like many similar devices manufactured of metal components, it is expensive, and if lost or stolen or misplaced, would represent an inconvenient financial loss to the owner.

By comparison, an injector constructed of plastic components is far less expensive, and this is of particular importance to many persons. In addition, an injector device is desired in which the amount of liquid in the syringe barrel can be easily ascertained. Frequently, individuals who use injector devices, particularly diabetics, cannot see the syringe scale too well. Consequently, in the case of a plastic injector, it would be very helpful to provide a magnifier of some type of enlarge the scale portion of the syringe. However, in the case of a metal injector, this is difficult and usually requires some type of significant design feature which tends to be expensive.

In many instances, diabetics do not use a specific amount of insulin at given times, but instead employ blood tests in conjunction with a kit to determine their blood sugar content, and hence their insulin dosage. This of course necessitates pricking the skin to obtain a small blood sample. It would be both convenient and less expensive if the same device which was used as an injector could also be used, albeit with some modifications, for obtaining a blood sample.

THE INVENTION

According to the invention, an injector device is provided, including an elongate exterior barrel portion having secured therein a depth gage which also functions as an aligning tube, through which the syringe and needle are aligned when they are fired. Upwardly of the exterior barrel there is mounted a spring loaded firing barrel into which the syringe and needle are mounted. The firing barrel is adapted to move through the upper portion of the exterior barrel together with the syringe and needle when they are fired.

In the loaded and cocked position, the firing barrel rests on an internal sleeve within the exterior barrel. When the internal sleeve is actuated by a release button, the firing barrel and attached syringe and needle are dislodged from the sleeve, and the syringe is projected through the exterior barrel and depth gage. The needle is then injected into the patient or user.

If the injector is used to produce a puncture and obtain a blood sample, the syringe is replaced by a striker cylinder. A puncture module comprising a spring loaded impact cylinder bearing a short disposable lancet is attached to the end of the depth gage. A much shorter firing stroke is realized with this system. This, together with the lancet size, will result in the lancet projecting just beyond the end of the puncture module, when the device is fired.

This enables the injector device to serve the dual purpose of injecting medication, or to produce a skin puncture for taking a blood sample for testing purposes.

BRIEF DESCRIPTION OF THE DRAWINGS

FIG. 2 is a sectional view in side elevation showing the injector, unloaded and uncocked;

FIG. 3 is an external view in side elevation, similar to FIG. 1 showing the injector and attached syringe, after cocking and after firing;

FIG. 4 is a sectional side elevation view showing the injector adapted for use with a skin puncture module, and including an impact cylinder to actuate the module; and, FIG. 5 is an external, perspective view of the skin puncture module, including a skin puncture, disposable lancet.

DESCRIPTION OF THE PREFERRED EMBODIMENTS

Figure 1:
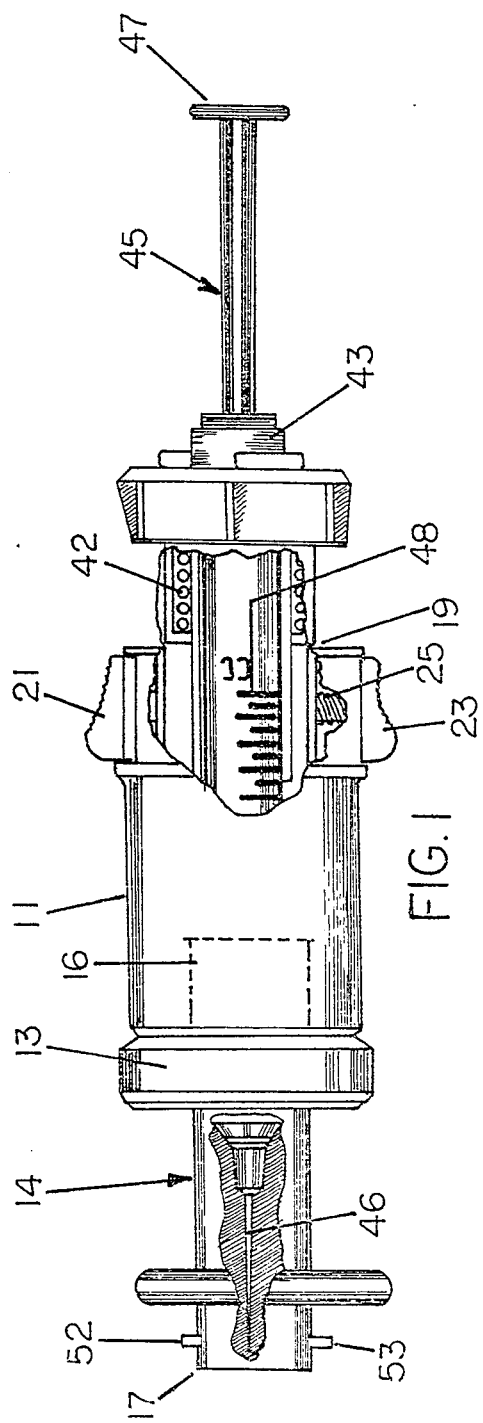
FIG. 1 is an external view in side elevation, partly broken away, showing the injector and attached syringe, prior to firing.

The injector device of this invention is shown in FIGS. 1 and 2, and comprises an exterior barrel 11 which is threaded 12 at its forward end for engaging an adjustable lock-nut 13. A depth gage 14 is mounted within the barrel 11 and secured therein by the combined effect of a tapered compression sleeve 15 and the action of the lock-nut 13. The depth gage 14 is adjustably mounted to permit a pre-selected length of needle to project therethrough when the injector is fired. The depth gage includes an aligning tube portion 16 which functions to align the syringe and needle as they are projected therethrough when the injector is fired. The depth gage also includes a desensitization ring 17 which rests against the user's body to enable accurate alignment of the device.

Within its rearward end, the exterior barrel 11 provides an internal sleeve 18 defining a shoulder 19. An extension 20 of the barrel wall functions to secure a trigger button 21 which actuates through a bore 22 in the extension 20. A stationary button 23 which is press fitted or bonded into a bore 24 in the extension 20 mounts a spring 25, and is positioned about 180° from the trigger button 21 to facilitate gripping and firing.

The internal sleeve 18 bears against the spring 25, and in the position shown in FIG. 2, pressures the trigger button a short distance 28 out of the bore 22; this distance 28 represents the trigger firing distance.

Inwardly of the internal sleeve 18 is a firing barrel 30 which is configured to provide spring loading chambers 31, 32 having biasing springs 33, 34. The firing barrel 30 provides upstanding walls 35, 36 which in conjunction with housings 37, 38 form the chambers 31, 32. The ends 35a, 36a of the walls 35, 36 are biased against the inner walls of the housings. Hence, whether retracted or after firing, the springs 33, 34 and the firing barrel 30 will always secure the syringe under tension. The syringe 45, including a needle 46 and plunger 47 is secured under this tension by syringe holder elements of the device, one element 43, being shown. These items are illustrated in FIGS. 2 and 4.

A stationary shaft 40 is positioned centrally of the injector, and its forward end 41 is bonded to the exterior barrel 11. The firing force for the firing barrel 30 is provided by a spring 42 secured between shaft 40 and the firing barrel 30.

As shown in FIGS. 1, 2 and 4, when the trigger button 21 is pressed, it will be moved inwardly against the bias of spring 25 and dislodge the firing barrel 30 from the shoulder 19. The spring loading 42 will then project the firing barrel 30 forwardly along with the attached syringe and needle, causing the needle 46 to penetrate the skin of the patient. The plunger 47 is then depressed manually to inject medication into the patient. If desired, a syringe scale 48 on the syringe 45 may be better viewed by a magnifying window 49 formed on the exterior of the barrel 11.

FIGS. 4 and 5 show the injector employed as a lancet device for obtaining blood samples. The syringe is replaced by a striker 50 which is attached and actuated in the same manner. With the depth gage 14 in the fully retracted position, the lancet module 51 is mounted thereon via bayonet elements 52, 53.

The lancet module comprises a body portion 55 and a spring loaded lancet holder 56, which is upwardly biased by a spring 57, as shown. A disposable lancet 58 in a mounting 59 is removeably mounted within the lancet holder 56.

When the striker is fired, the lancet will be moved forwardly to puncture the user and produce a small amount of blood for test purposes. The spring bias will then retract the lancet from the user back into the lancet holder, after which the lancet may be removed and discarded.

The injector device of this invention may be manufactured of inexpensive injection molded or extruded plastic components, such as LEXAN polycarbonate resin, and this reduces its cost considerably. Also, the device is easy to manipulate, and its dual function facilitates its use with little additional expense or training.

We claim:
1. A plastic injection device comprising:
   a. an elongate, exterior hollow barrel;
   b. a hollow, cylindrically-shaped depth gage means having a rearward end slidably received within the forward end of the exterior barrel such that the forward end of the depth gage means protrudes from the barrel;
   c. a cylindrically-shaped spring loaded firing barrel, including first spring loading means positioned at the rearward end of the exterior barrel for projecting the firing barrel forward, the spring loading means of the firing barrel being axially disposed between the firing barrel and the exterior barrel;
   d. an inwardly biased, spring loaded sleeve, including second spring loading means, said sleeve being mounted rearwardly and within the exterior barrel, the forward end of the firing barrel when cocked, resting on the said sleeve;
   e. an inwardly moveable firing button mounted on the exterior barrel for biasing the spring loaded sleeve outwardly against the force of the second spring loading means, the firing button being positioned opposed to the second spring loading means of the said sleeve;
   f. striker holder means mounted at the rearward end of the firing barrel for removeable attachment with a lancet striker means;
   g. spring loading means to maintain a lancet striker under tension on the striker holder means; and,
   h. a lancet module removably mounted at the forward end of the depth gage, the module comprising a rearwardly biased lancet holder, including a spring biasing means adapted to support a removeable lancet mounting and attached lancet; whereby:
      i. when the firing barrel is retracted against the force of the first spring loading means, it rests in a cocked position, on the spring loaded sleeve;
      ii. when the firing button is depressed inwardly, it outwardly biases the spring loaded sleeve and dislodges the firing barrel and thereby projects the lancet striker through the exterior barrel and depth gage to impact the lancet module against the force of the lancet spring biasing means, and thereby projects the lancet module forwardly and punctures a user's skin with the lancet;
      iii. the depth gage aligns the striker as it passes therethrough and adjusts the puncture depth of the lancet needle.
2. A lancet module, including a lancet needle, for producing a skin puncture and obtaining a blood sample, the module being adapted for attachment to a firing assembly, and including a hollow body portion, a rearwardly biased, spring loaded lancet holder slidably mounted within the hollow body portion and supported thereby, a lancet mounting and the attached said lancet being removovably connected to the lancet holder, whereby impact with a striker element of the firing assembly will project the lancet holder against the force of the spring loading means, and cause the lancet needle to puncture a user's skin, and then retract to its initial firing position.

* * * * *